United States Patent [19]

Manley et al.

[11] 4,019,133

[45] Apr. 19, 1977

[54] CORROSION DETECTING AND MONITORING APPARATUS

[75] Inventors: Robert E. Manley, Lower Burrell; John D. McCoy, Gibsonia, both of Pa.

[73] Assignee: Gulf Research & Development Company, Pittsburgh, Pa.

[22] Filed: Dec. 29, 1975

[21] Appl. No.: 644,968

[52] U.S. Cl. .......................... 324/65 CR; 324/71 R
[51] Int. Cl.² ................................. G01R 27/02
[58] Field of Search ........... 324/65 CR, 71 E, 71 R; 73/86

[56] References Cited

UNITED STATES PATENTS

| | | |
|---|---|---|
| 2,851,570 | 9/1958 | Schaschl .......................... 73/86 X |
| 2,956,225 | 10/1960 | Marsh et al. ..................... 324/71 R |
| 3,104,355 | 9/1963 | Holmes et al. ................... 324/71 R |

Primary Examiner—Stanley T. Krawczewicz

[57] ABSTRACT

A corrosion detector for determining the corrosivity of a fluid and the ability of a metal to withstand the corrosive tendencies includes a tubular test specimen and a reference specimen. The two specimens are of the same composition and configuration over the length of the test specimen over which measurements are made. Means are provided for maintaining the two specimens at a temperature within less than 1° F. of each other. The corrosive fluid is passed through the test specimen. An alternating current is passed through the test specimen and reference specimen and the change in resistance of the test specimen relative to the reference specimen is measured in a phase sensitive Wheatstone bridge circuit to determine the extent of corrosion.

10 Claims, 3 Drawing Figures

CORROSION DETECTING AND MONITORING APPARATUS

BACKGROUND OF THE INVENTION

1. Field of the Invention

This invention relates to the detection of corrosion and more particularly to apparatus for measuring and monitoring corrosion of metallic pipe or other metallic conduits through which fluids flow.

Much industrial equipment, such as pipelines, oil refineries and chemical and power plants require the flow of fluids through various types of metallic conduits. Often the fluids are at high temperature and sometimes the fluids are highly corrosive. Replacement of equipment or protection of equipment from corrosion constitutes an important part of the operating costs of such equipment. If the fluids are inflammable or otherwise hazardous, it is important to avoid failure of the conduits to avoid damage to other equipment, danger to operating personnel, and expensive shutdowns. Automatic detection and/or monitoring of corrosion of the conduits helps to avoid failure of the conduits.

2. Description of the Prior Art

A wide variety of corrosion detectors has been developed in an attempt to provide an accurate indication of the corrosion of equipment by fluids with which they are in contact. Such equipment generally includes a test specimen which is suspended in the corrosive fluid. The test specimen most frequently is a thin plate or wire suspended in the fluid whereby the fluid attacks the outer surface of the test specimen and the extent of corrosion is determined by measuring the loss of metal in the test specimen. The simplest and most direct method of measuring the loss of metal is by weighing the test specimen, but that method requires interruption of the corrosion test while the test specimen is withdrawn from the corrosive atmosphere, cleaned and weighed. Another method of measuring the loss of metal caused by corrosion is to measure the increase in the resistance to flow of an electric current through the test specimen. In those devices in which the outer surface of the test specimen is exposed to the corrosive fluid, sealing the specimen without introducing stray galvanic electric currents and protecting the electric leads from the corrosive fluid have been difficult. Moreover, use of thin plates or wires as test specimens does not simulate the conditions to which pipes are exposed in use.

Because the changes in electrical conductivity or resistance of the test specimen are small, accurate measurement of the resistance is essential in a corrosion detecting device. One method that has been used in an attempt to provide accurate measurement has been to compare in a Wheatstone bridge type circuit the electrical resistance of the test specimen with the electrical resistance of a reference specimen that is not exposed to the corrosive fluid. If the test specimen is a ferromagnetic material, such as carbon steel, it is important to avoid unsymmetrical electromagnetic effects. In many of the corrosion detection devices heretofore available, the lack of symmetry of the test specimen and the reference specimen can introduce electromagnetic effects that interfere with or prevent accurate measurements of the resistance. Although some of the electromagnetic effects can be avoided by passing a direct current through the specimens, detrimental thermoelectric effects may be introduced into measurement circuits using a direct current.

Other errors can be introduced into the corrosion monitoring devices of the prior art by failure to maintain the reference specimen and the test specimen at substantially the same temperature. The temperature of the reference specimen should not differ from the temperature of the test specimen by more than 0.5° F. and in no event more than 1° F. If the reference specimen is positioned at some distance from the test specimen or in a different environment, errors in measurement of the resistance of the test specimen may be introduced by difference in temperature between the test specimen and the reference specimen as well as by lack of the necessary symmetry in the system.

Corrosion detecting and monitoring apparatus are disclosed in:

U.S. Pat. No. 2,484,279 by Folz on 10-11-49
U.S. Pat. No. 3,080,747 by Kerst on 3-12-63
U.S. Pat. No. 3,155,933 by Rohrback et al on 11-3-64
U.S. Pat. No. 3,197,698 by Schaschl et al on 7-27-65
U.S. Pat. No. 3,222,920 by Marsh et al on 12-14-65
U.S. Pat. No. 3,320,570 by Lied, Jr. on 5-16-67

SUMMARY OF THE INVENTION

This invention resides in corrosion detection means which include a tubular test specimen through which a corrosive fluid flows. A reference specimen that is substantially identical to the test specimen in shape as well as composition is positioned adjacent to and electrically insulated from the test specimen. The corrosive fluid does not contact the reference specimen. Means are provided to maintain the test specimen and reference specimen at substantially the same temperature. An alternating current is passed both through the test specimen and reference specimen and the electrical resistance of the two specimens compared in a phase sensitive Wheatstone bridge.

DESCRIPTION OF PREFERRED EMBODIMENT

Figure 1:
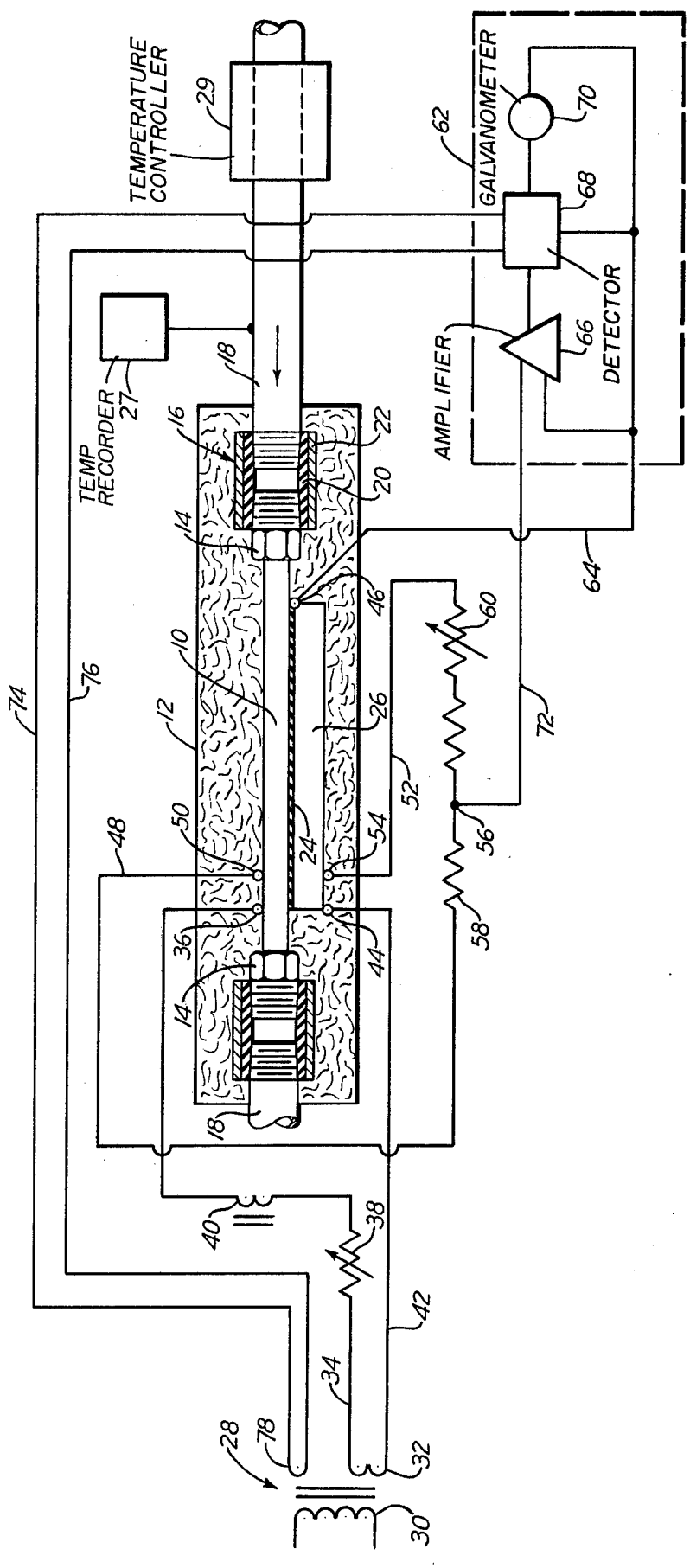
FIG. 1 is a diagrammatic illustration of an embodiment of the corrosion detecting apparatus of this invention suitable for use at low temperatures.

Referring to FIG. 1 of the drawings in which an embodiment of the invention suitable for use at relatively low temperature to measure the corrosivity of a fluid or the resistance of a metal to corrosion by a fluid is illustrated, a tubular test specimen 10 is shown encased within a thermally insulated housing 12. The ends of the test specimen 10 are provided with bushings 14 which screw into insulated couplings 16. Insulated couplings 16 electrically insulate the test specimen from pipe 18 through which the corrosive fluid is delivered into and from the test specimen. Pipe 18 may carry a slip stream withdrawn from the main stream of a process or may actually carry the main stream of corrosive fluid. Insulating couplings 16 are of a suitable electrically insulating material such as a phenolic plastic material 20 encased within a steel retainer 22 which gives the coupling the necessary physical strength. Because the embodiment illustrated in FIG. 1 is used at low temperatures which the phenolic plastic within coupling 6 can withstand, the couplings 16 are within the housing 12.

Immediately adjacent to the test specimen 10 but electrically insulated therefrom by suitable insulation 24 is a reference specimen 26. It is preferred that reference specimen 26 be separated from test specimen 10 only by the electrical insulation 24. The thermal insulation within the housing 12 and the close proximity to the test specimen maintain the reference specimen at a temperature very close to, preferably within 0.5° F., still more desireable within about 0.1° F. and in any event within 1° F., the temperature of the test specimen. If the temperature of the corrosive fluid changes slowly even though over a substantial range, the desired identity of temperature can be maintained. It is desirable that a temperature recorder 27 be provided to indicate the rate of change in the fluid temperature. A temperature controller 29 may be provided at the inlet to maintain a constant temperature or reduce the rate of change of the fluid temperature. Temperature controller 29 can be of conventional construction with means to heat or cool the fluid in pipe 18 to maintain an acceptable rate of change in the temperature.

Different ferromagnetic metals such as different types of carbon steel may vary substantially in changes of ferromagnetic properties and resistance with changes in temperature. Moreover, the rate of corrosion of different metals may not change at the same rate with changes in temperature. It is preferable that the test specimen be of the same metal as the metal that will be in contact with the corrosive fluid in a contemplated industrial or commercial apparatus, although in some instances correlation of the rate of corrosion of one metal with the rate of corrosion of a second metal permits use of a test specimen of one metal for prediction of the rate of corrosion of a different metal. Reference specimen 26 is a section of tubing or pipe of the same composition as the test specimen. To obtain the symmetry necessary for accurate measurement of the resistance, the reference specimen should be a tube of the same diameter as the test specimen and have a length over which the resistance is measured substantially the same as in the test specimen. The pipe 18 is provided with suitable flow control means such as pumps and valves, not shown, to permit regulation of the flow rate through the test specimen preferably to produce conditions of turbulence in the specimen corresponding to the conditions that exist in the apparatus processing the corrosive fluid.

An AC voltage preferably of about 5 to 10 millivolts is applied to the test specimen for measuring the changes in electrical resistance of the test specimen during the period of monitoring. Referring again to FIG. 1, a transformer 28 having a primary coil 30 connected, for example, to a 60 cycle AC source has a secondary coil 32. The secondary of the transformer is connected through a lead line 34 to a contact 36 on the test specimen 10. Connected in the lead line 34 is a variable resistor 38 and a choke 40. Choke 40 introduces an inductance that produces a phase difference at a detector instrument 68 in the Wheatstone bridge circuit. The other line 42 from the secondary 32 of the transformer is connected at contact 44 to the reference specimen 26. Reference specimen 26 and the test specimen 10 are electrically connected by a contact 46 at tne end remote from contacts 24 and 26 to connect the two specimens in series to form one side of a Wheatstone bridge connection for indicating resistance changes. The other leg of the Wheatstone bridge consists of a line 48 connected to the test specimen at contact 50 and a line 52 connected to the reference specimen at contact 54. Lines 52 and 48 are connected at contact 56. Line 48 includes a resistor 58 of fixed resistance between contacts 50 and 56 and line 52 includes a variable resistor 60 between contacts 54 and 56.

Contacts 46 and 56 are connected to conventional instrumentation for resistance measurement within broken lines 62 in FIG. 1. In the particular instrumentation shown, a lead line 64 from contact 46 is connected to an indicating circuit which includes an amplifier 66, the detector 68 and a galvanometer 70. A lead line 72 from contact 56 is also connected into the instrumentation circuit in a manner such that a difference in phase voltage between contacts 46 − 56 and 74 − 76 will be indicated by the galvanometer 70. A reference voltage is supplied to the detector 68 by lines 74 and 76 from a secondary coil 78 of transformer 28. The particular instrumentation used in combination with the Wheatstone bridge connection of the test and reference specimens and resistors 58 and 60 is not a part of this invention.

In the operation of the apparatus illustrated in FIG. 1, the test specimen 10 is connected to tubing 18 and the corrosive fluid passed through tubing 18 and the test specimen. The variable resistor 38 is adjusted to provide for the current to the resistance measuring instrumentation for the Wheatstone bridge circuit. Variable resistor 60 is then adjusted to give a zero reading at the galvanometer 70. If the temperature recorder 27 indicates that the temperature of the fluid is changing at a rate too high to permit accurate determination of the resistance of the test specimen, readings are delayed until the temperature is sufficiently stable. The flow of corrosive fluid through the test specimen is continued. Corrosion of the test specimen will result in a gradual increase in its resistance. The variable resistor 60 is adjusted to maintain a zero deflection at galvanometer 70. The resistance of the test specimen at any time during the test can then be calculated from the Wheatstone bridge formula:

R(test specimen)/R(reference specimen) = R58/R60

The change in electrical resistance is the direct result of the reduction in the metal available to conduct the current as a result of the corrosion of the metal, and can be correlated to give an index of the corrosivity of different fluids or of the ability of a metal to resist corrosion by the fluid.

Figure 2:
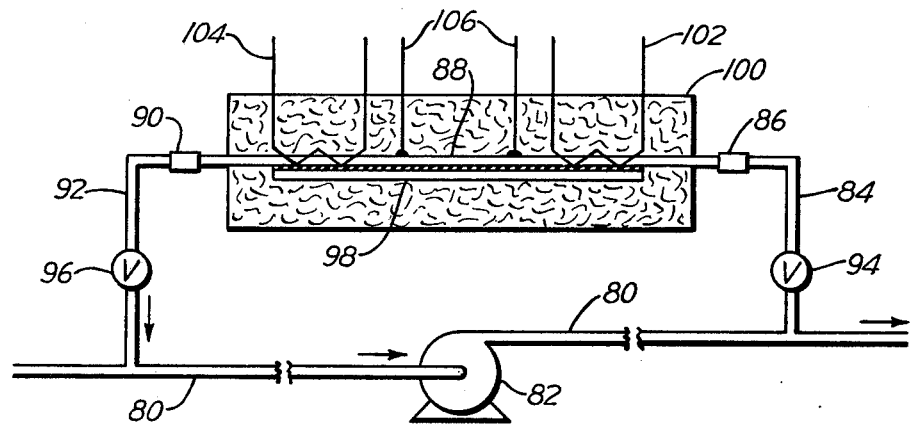
FIG. 2 is a diagrammatic illustration of an arrangement of the corrosion detecting apparatus utilizing a slip stream withdrawn from a flowing stream of a corrosive fluid.

The embodiment illustrated in FIG. 2 shows an arrangement for measuring the change in resistance of a test specimen resulting from flow of a corrosive liquid through the specimen at temperature exceeding the maximum temperatures at which the insulating coupling can be used. The apparatus can be used to measure the corrosivity of fluids at temperatures as high as 1000° F. (537° C.). In the embodiment illustrated in FIG. 2, the corrosive fluid is moved through a pipe 80 by a pump 82. A sample line 84 connected into pipeline 80 downstream of pump 82 is connected through an insulating coupling 86 to a test specimen 88. The discharge end of the test specimen 88 is connected by means of an insulating coupling 90 to a return line 92 which returns the corrosive fluid to pipe 80 upstream of pump 82. Valves 94 and 96 in sample line 84 and return line 92, respectively, permit control of the rate of flow through the test specimen.

Immediately adjacent test specimen 88 and electrically insulated therefrom in a manner similar to that described for the embodiment illustrated in FIG. 1 is a reference specimen 98. Both the test specimen and reference specimen are enclosed within a thermally insulated housing 100 to maintain the two specimens at substantially identical temperatures. Heating means indicated diagrammatically by reference numeral 102 are provided within the housing 100 between coupling 86 and the test specimen to raise the temperature of the corrosive fluid to the temperature at which the information concerning its corrosivity is required. It is contemplated that that temperature will be higher than the maximum temperature at which the insulating couplings 86 and 90 can be used. The corrosive fluid passing through the test specimen downstream from the test section of the specimen is cooled by suitable means indicated by reference numeral 104 before passing through insulating coupling 90. The test specimen 88 and reference specimen 98 are connected to suitable resistance measurement instrumentation similar to that disclosed in FIG. 1. Lead lines 106 are used in FIG. 1 to indicate the connection to the resistance instrumentation.

Figure 3:
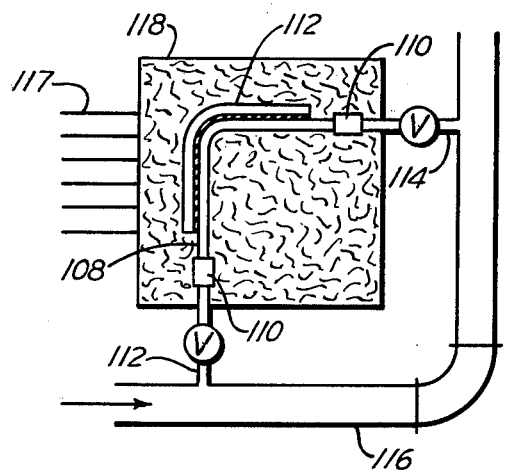
FIG. 3 is an embodiment of the invention for monitoring corrosion of a curved pipe section.

In the embodiment diagrammatically illustrated in FIG. 3, the test specimen is designed to simulate the corrosion that occurs in a right angle bend. The test specimen 108 is connected by insulating couplings 110 between a sample line 112 and a return line 114. Sample line 112 and return line 114 are connected into a pipe 116 through which the corrosive fluid flows. Test specimen 108 is enclosed within insulated housing 118. A reference specimen 112 having the same shape and of the same material as test specimen 108 is positioned within the housing adjacent the test specimen and is electrically insulated therefrom. Lead lines indicated diagrammatically by reference numeral 117 are connected to resistance measuring instrumentation similar to that disclosed in FIG. 1.

An important feature of the corrosion detector of this invention is the symmetry of the test specimen and reference specimen. When the metal in the test specimen is a ferromagnetic material, corrosion detectors heretofore available that apply an AC voltage developed an inductive effect which introduced erroneous signals into the system. The symmetry of the system resulting from the identity in shape and composition of the two specimens and their effectively same position minimizes inductive effects and provides an instrument of high sensitivity that give reliable measurement a few hours after flow through the test specimen begins. The positioning of the test specimen and the reference specimen very close together further results in a symmetry of the electrical leads to the Wheatstone bridge circuit.

It is usually desirable to use the instrument repeatedly for determination of the corrosivity of different fluids. The flow-through tubular test specimen can be easily cleaned and the surface prepared for determining the effects of changes in the fluid flowing through the tube or the effect of changes in processing conditions. The flow-through tubular specimen greatly simplifies attachment of electrical lead lines to the test specimen and completely eliminates the problem of protecting the lead lines and sealing the opening through which the lead line emerges from the pipe in which the wires or flat plates of the prior art devices are suspended. Location of the reference specimen outside of but immediately adjacent to the test specimen eliminates the problem of coating the reference specimen to protect it from the corrosive fluid.

The corrosion detector and monitoring apparatus of this invention can be used to determine the corrosivity of fluids over a wide range of temperature. If the temperature of the corrosive fluid in the processing apparatus exceeds the maximum temperature at which the insulating couplings can be used, suitable heating, cooling and temperature control devices are provided to raise the temperature of the corrosive fluid to the desired level between the inlet insulating coupling and the portion of the test specimen between the electrical contacts for the leads to the resistance measurement instrumentation and then to lower the temperature of the corrosive fluid before it reaches the outlet insulating coupling.

We claim:

1. Apparatus for measuring the rate of corrosion of a ferromagnetic metal by a flowing fluid comprising a tubular test specimen of the ferromagnetic metal, means for flowing the fluid through the test specimen, a tubular reference specimen of the ferromagnetic metal adjacent to the test specimen, said reference specimen being of substantially the same length, diameter and wall thickness as the test specimen, electrical insulation separating the test specimen and the reference specimen, a housing enclosing the test specimen and the reference specimen, thermal insulation within the housing around the test specimen and the reference specimen adapted to maintain the temperature of the specimens within 1° F. of one another, an alternating current source connected to the test specimen and the reference specimen to pass a current therethrough, and electrical leads attached to the outer surface of the test specimen and to the reference specimen connecting the specimens in a Wheatstone bridge circuit for measuring the resistance of the test specimen relative to the reference specimen to indicate the extent of corrosion of the test specimen.

2. Apparatus as set forth in claim 1 characterized by electrically insulating couplings connecting the ends of the test specimen to the means for passing the fluid through the test specimen to electrically insulate the test specimen from said means.

3. Apparatus as set forth in claim 2 characterized by the insulating couplings being outside of the housing, and temperature control means within the housing adapted to adjust the temperature in the test specimen to the temperature at which knowledge of the rate of corrosion is desired.

4. Apparatus as set forth in claim 2 characterized by the Wheatstone bridge circuit being a phase sensitive circuit.

5. Apparatus as set forth in claim 2 including a temperature recorder constructed and arranged to indicate the rate of change of temperature of the fluid flowing through the test specimen.

6. Apparatus as set forth in claim 2 characterized by temperature control means in the means for passing the fluid through the test specimen adapted to maintain the fluid delivered to the test specimen at a substantially constant temperature.

7. Apparatus as set forth in claim 2 characterized by the thermal insulation being adapted to maintain the temperatures of the test specimen and reference specimen within 0.1° F. of one another.

8. Apparatus as set forth in claim 2 characterized by the test specimen being curved and the reference specimen having substantially the same shape as the test specimen.

9. In apparatus for measuring the rate of corrosion of a test specimen by a flowing fluid wherein the resistance of a test specimen is periodically compared in an alternating current Wheatstone bridge circuit with the resistance of a reference specimen, the improvement comprising a tubular test specimen through which the fluid flows, a tubular reference specimen of the same diameter and composition as the test specimen adjacent the test specimen, means for flowing the fluid through the test specimen, electrical insulation between the test specimen and the reference specimen, and means for maintaining the temperatures of the test specimen and the reference specimen within 0.5° F. of one another.

10. Apparatus for indicating the rate of corrosion of a metal by a flowing fluid comprising a tubular test specimen of the metal; means for flowing the fluid through the test specimen; means around the test specimen for adjusting the temperature of the fluid flowing through the test specimen; a reference specimen of the metal adjacent to the test specimen; electrical insulation separating the test specimen and the reference specimen; a housing enclosing the test specimen, reference specimen and means for adjusting the temperature; thermal insulation within the housing around the test specimen and the reference specimen adapted to maintain the temperature of the specimens within 1° F. of one another; an alternating current source connected to the test specimen and the reference specimen to pass a current therethrough; and electrical leads attached to the outer surface of the test specimen and to the reference specimen connecting the specimens in a Wheatstone bridge circuit for measuring the resistance of the test specimen relative to the reference specimen to indicate the extent of corrosion of the test specimen.

* * * * *